United States Patent [19]

Mencke et al.

[11] Patent Number: 4,829,001

[45] Date of Patent: * May 9, 1989

[54] ENZYMATIC NEUTRALIZATION OF HYDROGEN PEROXIDE

[75] Inventors: Arlene J. Mencke, St. Paul, Minn.; Carol E. Hendrickson, St. Joseph Township, County of Croix, Wis.; Rosa Uy, St. Paul, Minn.

[73] Assignee: Minnesota Mining and Manufacturing Company, St. Paul, Minn.

[*] Notice: The portion of the term of this patent subsequent to Jul. 12, 2005 has been disclaimed.

[21] Appl. No.: 796,272

[22] Filed: Nov. 8, 1985

[51] Int. Cl.$^4$ .................... C12N 11/08; C12N 11/14; C12N 11/02

[52] U.S. Cl. .................................. 435/264; 435/180; 435/176; 435/177

[58] Field of Search ............... 435/262, 264, 181, 174, 435/176, 177, 179, 180, 188, 192, 288; 422/28, 30, 56, 61; 424/443, 94.4; 134/27, 2, 93

[56] References Cited

U.S. PATENT DOCUMENTS

| 3,282,702 | 11/1966 | Schreiner ................................ 99/54 |
| 3,715,278 | 2/1973 | Miller . |
| 3,928,143 | 12/1975 | Coughlin et al. ............... 435/176 X |
| 4,025,667 | 5/1977 | Tomb et al. .......................... 427/215 |
| 4,038,485 | 7/1977 | Johnston et al. ........................ 435/4 |
| 4,098,645 | 7/1978 | Hartdegen et al. .................... 195/68 |
| 4,115,198 | 9/1978 | Coughlin et al. .................... 435/176 |
| 4,118,536 | 10/1978 | Beardsley et al. ................. 528/23 X |
| 4,210,722 | 7/1980 | Silver .................................. 435/176 |
| 4,258,133 | 3/1981 | Mirabel et al. ....................... 435/176 |
| 4,448,884 | 5/1984 | Henderson ....................... 435/176 X |
| 4,473,550 | 9/1984 | Rosenbaum et al. ............. 435/78 X |
| 4,564,532 | 1/1986 | Henderson ....................... 435/176 X |
| 4,585,488 | 4/1986 | Giefer ............................. 435/264 X |
| 4,588,586 | 5/1986 | Kessler et al. ................... 435/264 X |
| 4,748,992 | 6/1988 | Giefer .................................. 134/84 |
| 4,757,014 | 7/1988 | Hendrickson et al. ............. 435/176 |

FOREIGN PATENT DOCUMENTS

| 60652 | 3/1987 | Australia . |
| 0046613 | 3/1982 | European Pat. Off. . |
| 0082798 | 6/1983 | European Pat. Off. . |
| 0155505 | 9/1985 | European Pat. Off. . |
| 2573772 | 5/1986 | France . |
| 8607264 | 12/1986 | World Int. Prop. O. . |

OTHER PUBLICATIONS

Osborn et al, Biotechnology and Bioengineering, vol. 24, No. 7, Jul., 1982, pp. 1653–1669.

Primary Examiner—Robert J. Warden
Assistant Examiner—Randall E. Deck
Attorney, Agent, or Firm—Donald M. Sell; Walter N. Kirn; Lorraine R. Sherman

[57] ABSTRACT

A method for disinfecting a medical device comprising the steps of immersing a medical device in a hydrogen peroxide solution for a time sufficient to disinfect said device, decomposing any residual hydrogen peroxide by use of a catalytically effective amount of a protein capable of decomposing hydrogen peroxide, said protein being immobilized on a composite article, said composite article comprising in sequence a support, a layer of protein immobilizer compound, and a biologically active protein. The surface modification treatment is a gelled network of inorganic oxide particles or a plasma treatment.

19 Claims, No Drawings

ENZYMATIC NEUTRALIZATION OF HYDROGEN PEROXIDE

FIELD OF THE INVENTION

This invention relates to a method for disinfecting a medical device comprising enzymatic neutralization of a hydrogen peroxide solution. In another aspect, a kit for use in the method of the invention is disclosed. The medical device can be, for example, a contact lens.

BACKGROUND OF THE INVENTION

Soft contact lenses, such as those made from plastic gel materials, e.g., hydroxyethyl methacrylate (HEMA) or its analogues and ethylene glycol dimethacrylate (EGMA) or its analogues, are replacing traditional hard contact lenses as the lenses of choice for many people. Soft lenses are more comfortable to wear than the hard lenses, but they pose a more complex problem than the hard lenses when it comes to care and maintenance. Hard lenses may be cleaned and disinfected relatively easily. Since they do not absorb appreciable amounts of water and aqueous solutions, the use of somewhat harsh cleaning and disinfecting agents is not generally a problem.

Soft lenses, on the other hand, require greater care in cleansing and storage. The solutions useful with hard lenses often are not compatible with soft lenses because the soft lenses tend to absorb or concentrate certain constituents of the formulation, which could result in damage to the lens or harm to the eye of the user.

Similarly, soft lenses are more vulnerable to microbial contamination than are hard lenses. The nutritive effect of body fluids, and the protective effect of nicks or imperfections in soft lenses, can serve to augment the growth of microbes.

While it is relatively easy to find antimicrobial agents active against such microbial contaminants, it is more difficult to find an antimicrobial agent that is compatible with soft contact lenses, and more difficult yet to find one that is non-irritating and safe for contact with the human eye.

Antimicrobial agents which are suitable for external contact or even for injection or ingestion are often unsuitable for use in eye care due to the particularly sensitive nature of the tissues in the eye. For example, they might be unsuitable because of direct toxicity to the eye, poor solubility in aqueous vehicles, eye irritation or ocular allergenic effects, absorption or binding by the contact lens, or chemical interaction with the contact lens or even its plastic lens case.

An antimicrobial agent useful for ocular applications must not contribute to any of the above problems. In particular, it must satisfy two basic requirements, i.e. that it be non-irritating to the eye, and that it be effective against a wide variety of microorganisms.

Hydrogen peroxide is a very effective antimicrobial agent which is currently used to disinfect contact lenses, including soft contact lenses. Although it is potentially irritating to the eye if significant residues are contained on or in the contact lens, it is known that hydrogen peroxide can be removed by soaking a disinfected lens in a solution containing a catalyst such as platinum oxide which catalyzes the decomposition of hydrogen peroxide. Solutions of the enzyme catalase have also been added to decompose hydrogen peroxide in solutions previously used to sterilize contact lenses. See, for example, European Patent application No. 82710055.3. However, if introduced into a solution with a lens, catalase can bind to the lens, compounding the familiar protein deposit problem associated with the use of contact lenses.

It is known in the art that certain proteins can be immobilized on specific supports. U.S. Pat. No. 4,098,645 describes the immobilization of enzymes on isocyanate end-capped polyurethane polymer foams, and catalase is one of a long list of enzymes listed and claimed.

U.S. Pat. No. 3,282,702 describes certain classes of polymeric carriers which bind catalase for the purpose of providing articles for removing hydrogen peroxide from potable liquids.

U.S. Pat. No. 4,210,722 describes a method of immobilizing a protein such as an enzyme on a polar support in a variety of configurations which may be glass, ceramic, inorganic oxide, etc. comprising applying a layer of a polymer having repeating units containing a beta-hydroxy-alkyleneamine moiety such as the dimethylamine adduct of epoxidized polybutadiene to a polar support and contacting the treated support with an aqueous solution of the protein. One of the enzymes exemplified in this patent is catalase.

SUMMARY OF THE INVENTION

Briefly, the present invention provides a method for disinfecting a medical device comprising the steps of immersing a medical device in a hydrogen peroxide solution for a time sufficient to disinfect the device, decomposing any residual hydrogen peroxide by use of a catalytically effective amount of a protein capable of causing decomposition of hydrogen peroxide, the protein being immobilized on a composite article, the composite article comprising in sequence (1) a support, (2) a layer of a protein immobilizer compound, and (3) a biologically active protein capable of causing decomposition of hydrogen peroxide.

In another aspect, a kit for use in the method of the invention is disclosed.

Optionally, in the method of the invention, the support can be subjected to a surface modification treatment prior to being coated with a protein immobilizer compound. A surface modification treatment can comprise a layer of a polar material capable of providing binding sites for the protein immobilizer compound or it can be a plasma treatment.

It has not previously been known that it is possible to achieve disinfection with hydrogen peroxide while simultaneously decomposing excess hydrogen peroxide by the use of the protein catalase immobilized upon a support. In particular, the use of catalase, immobilized upon a woven or nonwoven article, to decompose hydrogen peroxide has not been known. Immobilized proteins such as enzymes can retain a substantial portion of their biological activity even though bound to a support.

Surprisingly, it has been found that certain polymers, including polyalkylenes, commonly used to make nonwoven webs, can be used as supports for binding protein immobilizer compounds if they are first subjected to a surface modification treatment. It has not previously been known to treat woven and nonwoven webs for the purpose of providing binding sites for chemical additives to immobilize biologically active molecules Hydrogen peroxide systems which have been used to disinfect contact lenses may be classified by the number of containers used during the disinfection process and by the number of steps required to complete the disinfection process.

A two-container, two-step method involves separate, noncompeting reactions. In the first step lenses are put into a container containing an amount of hydrogen peroxide sufficient for disinfecting the lenses in a short period of time (about 10 minutes). In the second step, as is known in the art, the lenses are then transferred to a second container which contains a saline solution and a disc of platinum. The platinum disc catalytically converts the hydrogen peroxide into molecular oxygen and water. The lenses are soaked in the second container for four or more hours to remove the residual hydrogen peroxide from the lenses. Other systems which have been used to remove the hydrogen peroxide from the lenses can either include the use of a solution of sodium bicarbonate or the enzyme catalase in solution. These systems may use one or two containers but always require two steps: first a soak in hydrogen peroxide and second a neutralization step.

The two-step, two-container system is bulky, cumbersome and requires relatively large volumes of solutions. Two step, one-container systems are also bulky, cumbersome and require more than one solution. A problem arises when the wearer forgets the second step and does not neutralize the hydrogen peroxide in the lenses. The wearer then has lenses which are contaminated with hydrogen peroxide and are not suitable for use. It is, therefore, desirable to provide a system which uses only one container and one step to achieve the disinfection of the lenses and the neutralization of the hydrogen peroxide.

When a one-step system is used to disinfect contact lenses there are two competing reactions which must be controlled to achieve disinfection as well as neutralization. One reaction is the killing of the infectious organisms on the lenses by the hydrogen peroxide. The concentration of the hydrogen peroxide must remain at a high enough level for a period of time long enough to achieve disinfection. The second reaction is the conversion of residual hydrogen peroxide into water and molecular oxygen or other compounds. The conversion reaction must be slow enough to allow killing of the microorganisms but fast enough to neutralize substantially all of the hydrogen peroxide in a period of time suitable for having the lenses ready for use (usually four to six hours).

The present invention permits the use of a one-container, one-step system by controlling the amount of immobilized enzyme present. The amount of immobilized enzyme put into the container can be controlled by selecting the appropriate amount of support. A low amount of enzyme will cause a slow neutralization of hydrogen peroxide which will allow the disinfection to take place. If, on the other hand, a fast system for hydrogen peroxide disinfection is desired, a two-step system would be preferable: a larger concentration of enzyme can be put into the container after the 10-minute disinfecting soak and the larger amount of enzyme will neutralize the hydrogen peroxide very rapidly, reducing the total required time for disinfection from the usual four to six hours to one hour or less. A very fast system is highly desirable for patients wearing extended wear lenses who do not wish to leave their lenses out of their eyes for the four to six hour period required by products currently available.

The activity of the enzyme in neutralizing hydrogen peroxide can also be attenuated by use of controlled release technology. The webs, beads or porous filters of the invention may be coated with a slowly erodable polymer such as a cellulose derivative, poly(N-vinyl pyrrolidone) or poly(vinyl alcohol). The erodable polymer coating on the surface prevents the enzyme from neutralizing the hydrogen peroxide and slowly dissolves in the hydrogen peroxide solution. When the polymer coating has dissolved in the solution, the enzyme neutralizes the hydrogen peroxide at a rate proportional to the amount of active enzyme present.

The medical devices which can be disinfected in conjunction with the article of the invention can be any object which is used in or applied to the human body and which must be free of significant amounts of hydrogen peroxide after disinfection. Such articles include devices used in the eye which may require regular disinfection such as contact lenses. Other articles suitable for disinfection include medical and dental instruments, surgical staples, and implants of various types. An article and a method for immobilizing biologically active protein is disclosed in assignee's copending patent application U.S. Ser. No. 07/796,274, filed the same date as this application, now U.S. Pat. No. 4,757,014.

As used in this application:

"disinfecting" means to destroy, neutralize or inhibit the growth of infectious agents present;

"woven fibrous web" means a sheet or pad of interlaced strands of yarn;

"nonwoven fibrous web" means a sheet or pad of a random network of fibers;

"ceramic" means any inorganic nonmetallic material (includes metal and nonmetallic oxides) which requires the application of high temperatures at some stage in its manufacture but is not derived from a melt;

"ceramic-precursor" means a material capable of being converted to a ceramic by application of high temperatures;

"sol" means a colloidal dispersion of a finely divided solid phase in a liquid medium;

"polar layer" means a layer on the surface which is wettable by water;

"continuous" means a layer with virtually no discontinuities or gaps therein;

"gelled network" means an aggregation of colloidal particles linked together to form a porous three-dimensional network;

"particle" means spherical, non-spherical, and fibrillar particulate arrangements;

"primary particle size" means the average size of unagglomerated single particles of inorganic metal oxide;

"porous" means the presence of voids created by the packing of particles, the dried product preferably has an open porosity of between 25 and 70 percent;

"monolayer" means a thin layer approximately 10 to 250 angstroms thick, with the preferred thickness being in the range of 10 to 100 angstroms; and "mat" means unfused fibers;

"thermally bonded" means a mat of fibers that has been fused by heat at junction points (e.g., the sample was passed through heated 232° C. (450° F.) calendering rolls); and "embossing" means a mat of fibers thermally fused by imprnting a pattern on the mat.

DETAILED DESCRIPTION OF THE INVENTION

The present invention provides a method for disinfecting a medical device comprising the steps:
(a) immersing a medical device in a hydrogen peroxide solution for a time sufficient to disinfect said device,
(b) decomposing any residual hydrogen peroxide by use of a catalytically effective amount of catalase or peroxidase immobilized on a composite article, said composite article comprising in sequence:
  (1) a support,
  (2) a layer of a protein immobilizer compound, and
  (3) catalase or peroxidase.

For many uses it is desirable for a protein, once it has been immobilized on a support by means of a protein immobilizer, to be retained in its entirety or substantially in its entirety on the support so as to not contaminate another substance. Polar groups can provide binding sites which can interact with certain protein immobilizers. Such sites allow binding of the protein immobilizer to be maximized.

Catalase or peroxidase can be firmly attached with appropriate protein immobilizer compounds to inorganic oxide supports, such as glass, or polymers supports, for example, polyesters such as polyethylene terephthalate, without further modification of the support. When the support is in a configuration with high surface area, such as beads, sintered glass, glass wool, or ceramic fibers such as Nextel ™ (3M), enough active enzyme can be bound so that the composite article can be contained in a small volume and can be useful for contact lens disinfection systems.

Optionally, prior to being coated with a layer of a protein immobilizer compound, the support can be subjected to a surface modification treatment to provide binding sites for the protein immobilizer compound. A surface treatment can be a layer comprising a gelled network of inorganic oxide particles which, preferably, is a layer of porous ceramic-precursor material, or it can be a plasma treatment.

Supports useful in the present invention include polymeric or inorganic oxide materials in high surface area configurations such as beads and fibers.

Woven and nonwoven webs are useful as supports in the articles of the invention. Fibrous webs are desirable for use in the method of the invention because they provide large surface areas for binding protein. Woven webs are alternatives to nonwoven webs for the purposes of the invention. A wide variety of fiber diameters, e.g. 0.05 micrometer to 50 micrometers in diameter, preferably 0.1 to 20 micrometers, can be used in the composite articles of the invention. Any web thickness can be useful in specific applications, preferably 0.2 micrometer to 10 cm thick, most preferably, 0.1 mm to 1 cm in thickness.

Nonwoven fibrous webs are preferred in the practice of the invention. Nonwoven webs have several advantages over woven materials including high surface area, ease of manufacture, low material cost, and allowance for variation in fiber texture and fiber density. Also, the web properties, such as thickness and loft, can be varied to provide optimal surface area which can control the amount of enzyme in a given space. The preferred materials useful to prepare nonwoven fibrous web compositions of the invention include polymers and copolymers of monomers which form fibrous webs. Suitable polymers include polyalkylenes such as polyethylene and polypropylene, polyvinyl chloride, polyamides such as the various nylons, polystyrene, polyarylsulfones, polyvinyl alcohol, polycarbonate, polyacrylates such as polymethyl methacrylate, cellulosics such as cellulose acetate butyrate, polyesters such as poly(ethylene terephthalate), polyimides, and polyurethanes such as polyether polyurethanes, and combinations thereof. Nonwoven webs may also be prepared from combinations of co-extruded polymers such as polyester and polyalkylenes. Copolymers of the monomers which provide the above described polymers are also included within the scope of the invention. Nonwoven webs may also be combined webs which are an intimate blend of fine fibers and crimped staple fibers.

Fibrous webs of the invention can be prepared by methods known in the art. Nonwoven form webs may be prepared by melt-blowing as is known to those skilled in the art and described in, for example, U.S. Pat. No. 3,978,185 and V. A. Wente et al. "Manufacture of Superfine Organic Fibers", Naval Research Laboratories Report No. 4364, Naval Research Laboratories, Washington, D.C. (U.S. Document No. 111437) which are incorporated herein by reference. Alternative techniques such as solution-blowing can also be used as described, for example, in U.S. Pat. No. 2,571,457, which is incorporated herein by reference. The method used to prepare the nonwoven material is not critical.

Nonwoven webs can be embossed or thermally bonded, as is known in the art, to give integrity to the web. Pillowing of nonwovens is useful and is described in detail in U.S. Pat. Nos. 4,042,740 and 4,103,058. The nonwovens of these patents are useful in the present invention. Woven fibrous webs include any type of patterned or knitted fabric or pad.

Protein immobilizers useful in the method of the invention are any of the known polymers which adhere readily to polar supports and provide immobilization of proteins, such as enzymes, while preferably retaining substantially all of the biological activity of the protein.

Included among the suitable protein immobilizers and/or coupling agents are polymers having repeating units containing a beta-hydroxyalkyleneamine moiety, silane-functional compounds such as gamma-aminopropyltriethoxysilane and silane-treated polycarbodiimide polymers of U.S. Pat. No. 4,118,536. It is presently preferred to use polymers such as those described in U.S Pat. No. 4,210,722, the teaching of which patent is incorporated herein by reference. The polymers described as useful in that invention are generally useful in the present invention. A particularly preferred type of polymer described in the above patent is N,N-dialkylamine adducts of epoxidized polybutadiene such as the N,N-dimethylamine adduct of epoxidized polybutadiene. Although this reference discloses only water-soluble protein immobilizers, the present invention includes within its scope both water-soluble and organic solvent-soluble (e.g. toluene) protein immobilizers. Especially preferred polymers for practicing the invention are formed from amine adducts of epoxidized poly-cis-1,4-butadiene, epoxidized styrene/cis-1,4-butadiene, and polyglycidyl methacrylate wherein the amine can be a primary or secondary amine such as dimethylamine, diethylamine, morpholine, piperidine, or n-propylamine, as described in U.S. Pat. No. 4,210,722.

The $\beta$-hydroxyalkyleneamine-containing polymers have molecular weights ranging from 1000 to several million. However, the preferred molecular weight is in the range of 10,000 to 250,000. As molecular weight is increased above about 250,000, the aminated polymers create preparative problems.

Enzymes immobilized by, for example, β-hydroxyalkyleneamine-coated or silane-functional compound-coated on porous supports such as sintered glass (e.g., plates) or nonporous supports such as glass beads, and fibrous supports as described herein, are useful in the enzymatic decomposition of hydrogen peroxide. Examples of enzymes which can be strongly attached to the β-hydroxyalkyleneamine polymers and silane-treated polycarbodiimide polymers include catalase and peroxidase.

If the support does not effectively bind a protein immobilizer compound, the support surface may be treated with an appropriate coating or plasma.

In one embodiment, the fibrous support can be coated on its surface with a layer of a polar material capable of providing binding sites to the support surface. Such materials are wettable by water and include metal oxides, glasses, ceramics, ceramic-precursors, and clays. Silaceous materials such as sand, glass and quartz are generally suitable. Inorganic compounds such as oxides and barium ferrite are also considered suitable. Preferred of these optional materials are inorganic oxides which form gelled networks. Most preferably the optional polar layer is a virtually continuous, porous ceramic-precursor gel layer consisting of spherical particles preferably of 20 to 600 angstroms and most preferably of about 50 angstroms in diameter. These gels are preferred because they are found to bind readily to nonwoven webs. The amount of gel used will generally be about 0.06 to 0.15 grams per gram of nonwoven web.

The layer of optional inorganic oxide compound is substantially uniform in thickness and is substantially permanently adhered to the support, i.e. has a 180° peelback value of at least about 150 g/cm, preferably at least about 500 g/cm, as measured on a polyethylene terephthalate film. The dried coating is preferably from about 2 to 500 nm thick. Such coatings provide good adhesion. When the coating thickness is too great, the coating has reduced adhesion and flexibility and may flake off or form powder under mechanical stress.

In another embodiment, a plasma treatment utilizing an activated gas such as air, oxygen, carbon dioxide, argon, helium, nitrous oxide, water vapor, and the like, or combinations thereof, optionally, can be utilized as an alternative to a layer of polar material coated on the support, to provide a water-wettable or polar surface on the support.

In the process of the invention the fibrous support is optionally coated with a solution or suspension of colloidal inorganic oxide particles (sol) preferably having an average primary particle size less than about 200 angstroms (A), more preferably less than about 70 A. The sol preferably contains 0.2 to 15 weight percent, preferably about 0.5 to 6 weight percent, particles. At particle concentrations above 15 weight percent, the resulting coating may have reduced uniformity in thickness and exhibit reduced adhesion to the substrate surface. At concentrations below 0.2 weight percent, process inefficiencies result due to the large amount of liquid which must be removed.

It is presently preferred to use sols of ceramic-precursor materials, e.g. inorganic oxides, to treat the nonwoven polymer webs. Inorganic oxides particularly suitable for use in the present invention include colloidal silica particles, boehmite (alpha-$Al_2O_3 \cdot H_2O$), tin oxide ($SnO_2$), antimony oxide ($Sb_2O_5$), zirconium oxide ($ZrO_2$), and alumina-coated silica as well as other inorganic metal oxides of Groups III and IV of the Periodic Table and mixtures thereof. The selection of the inorganic oxide depends upon its ability to adhere to the support and provide adequate binding for the protein immobilizer compound.

Examples of commercially available inorganic oxides include colloidal silica sols (Nalco TM 2326 and Nalco TM 1034A, Nalco Chemical Co., Oak Brook, Ill.), dispersable alumina boehmite (Dispural and Pural, Condea Petrochemie GmbH; Catapal SB, Vista Chemical Co.), and alumina sol, (Nalco 1SJ-614), antimony oxide sol, (Nalco 1SJ-611), and alumina-coated silica sol, (Nalco 1SJ-613, Nalco Chemical Company).

The term "solution" as used herein includes dispersions or suspensions of finely divided particles of ultramicroscopic size in a liquid medium. The solutions used in the practice of this invention are clear to milky in appearance.

The optional coating solution may also optionally contain a surfactant to improve wettability of the solution on the support, but inclusion of an excessive amount of surfactant may reduce the adhesion of the coating to the support. Examples of suitable surfactants include nonionic surfactant trimethyl nonyl polyethylene glycol ether (Tergitol TMN-6, Union Carbide Corp.) and octylphenoxy polyethoxy ethanol (Triton X-100, Rohm and Haas Co.). Generally the surfactant can be used in amounts of up to about 0.5 weight percent of the solution.

Also, the optional coating solution may optionally contain a polymeric binder to aid in adhering the coating to the support. Useful polymeric binders include polyvinyl alcohol, polyvinyl acetate, polyesters, polyamides, polyvinyl pyrrolidone, copolyesters, copolymers of acrylic acid and/or methacrylic acid, and copolymers of styrene. The coating solution can contain up to about 20 weight percent of the polymeric binder based on the weight of the inorganic oxide particles. Useful amounts of polymeric binder are generally in the range of 1 to 15 weight percent.

Addition of various adjuvants, such as slip agents and processing oils, to the support material may reduce the adhesion of the coating to the support.

Coating may be carried out by standard coating techniques such as bar coating, roll coating, curtain coating, spraying, dipping, or other techniques evident to those skilled in the art. The substrae may be treated prior to coating to obtain a uniform coating using techniques such as corona discharge, flame treatment, and electron beam. Generally, no pretreatment is required.

The thickness of the optionally applied wet coating solution is dependent on the concentration of inorganic oxide particles in the coating solution and the desired thickness of the dried coating. The thickness of the wet coating solution is preferably such that the resulting dried coating thickness is from about 70 to 500 nm.

After soaking a nonwoven web in the coating solution of inorganic oxide particles the web is either dried at a moderately low temperature, generally less than about 200° C., or at room temperature, provided the drying time is sufficient to permit the coating to remove the water or organic solvent completely to provide good bonding of the oxides to the nonwoven webs. The drying temperature should be less than that at which the substrate degrades.

An alternative process for modifying the surface of woven and nonwoven webs is a plasma treatment. A plasma is generated by electrical discharge of the selected gas between two flat electrodes, at a reduced pressure. Direct current (D.C.) or alternating current (A.C.) radiofrequencies or microwave plasmas can be useful, preferably at 10 to 125 kilohertz. Gas pressures of 10 millitorr to 10 torr can be used, preferably 0.5 to 2.0 torr. Power ranges preferably are 10 to 400 watts or power densities in the range of 0.05 to 2.25 watts/cm$^2$.

Nonwoven or woven fibrous webs positioned between the two electrodes can be exposed to a plasma treatment from 1 second to 30 minutes, preferably 10 to 60 seconds.

Depending on the gas used, a plasma treatment provides the surface of the support with reactive, polar groups including hydroxy, ester, acid, carbonate, amine, peroxide and hydroperoxide groups. These groups are a source of binding sites for the protein immobilizer compound.

The process of the invention includes treating a woven or nonwoven fibrous web which is naturally polar or which optionally has been subjected to a surface modification treatment as previously described, with a coating of a protein immobilizer polymer. The protein immobilizer coating is provided by deposition of any of the protein immobilizer polymers described above, preferably in a monolayer. The polymer is deposited onto the polar support from a dilute aqueous solutions. Generally, solution containing 0.03 to 0.5 percent polymer (w/w) are used.

For example, the β-hydroxyalkyleneamine polymer can be deposited as a monolayer on the treated surface of the support, by immersing the support in a dilute aqueous solution of the polymer for 30 seconds to 24 hours, followed by a water wash. The support may be dried and stored or used immediately to contact an aqueous solution of the protein to be immobilized.

Deposition of the protein on the polymer-support composite comprising a fibrous support, optional polar material, and protein immobilizer compound is preferably accomplished by immersion of the composite in the protein solution which preferably is a buffered aqueous solution. The optimum concentration of the protein solution will vary depending on the protein immobilized. Generally, protein solutions in the range of 0.01 to 100 mg/mL will be used. Following an equilibration period of a few seconds to 24 hours, the composite is removed from the protein solution and washed with water and/or buffer until unbound protein is removed. The resulting composite can then be dried in air and/or over a desiccant. In some cases, lyophilization can be used.

Currently used systems for disinfecting, e.g., contact lenses, utilize two-container systems wherein the lens is first immersed in hydrogen peroxide solution in one container and then immersed in a solution containing a catalyst in a second container for the decomposition of residual hydrogen peroxide.

It is most convenient to use the method of the invention when a one-container system is used, and particularly for the disinfection of contact lenses. However, the method of invention wherein a two-container system is used is also novel, since suitable nonwoven articles upon which catalase is immobilized have not previously been known, and such articles have not previously been available for use in methods to disinfect objects such as contact lenses. Because of low cost the composite article of the invention can be part of a disposable kit. A kit useful in the method of the present invention can be re-used. It has been found that such a kit can be effective in the method of the invention even after 5 uses.

Objects and advantages of this invention are further illustrated by the following examples, but the particular materials and amounts thereof recited in these examples, as well as other conditions and details, should not be construed to unduly limit this invention.

The phosphate buffer used throughout the Examples, unless otherwise specified, is 0.01 M potassium dihydrogen phosphate, pH adjusted to 7.2 with 1N aqueous potassium hydroxide.

The catalase used throughout the Examples is commercially available catalase with activity (according to the manufacturer, Sigma Chemical Co.) of 40,000 International Units (IU) per milligram. However the activity was measured by a standard assay (described by Beers and Sizer, J. Biol. Chem. 195, 133 (1952)) wherein one unit of enzyme decomposes one micromole of hydrogen peroxide per minute at 15° C. at pH 7, to be 20,500 IU per milligram unless otherwise specified. All percents are by weight unless otherwise specified.

EXAMPLE

A 0.7 g wad of glass wool was soaked in 7 mL of a 0.06% aqueous solution of the dimethylamine adduct of epoxidized polybutadiene (DIMA), of molecular weight 92,000, prepared as described in U.S. Pat. No. 4,210,722, for about five hours at about 20° C. The solution was drained from the glass wool which was then soaked in 6 mL of a solution of 1.0 mg of catalase in 0.01M phosphate buffer, pH 7.0 for about sixteen hours. The glass wool was again drained of the solution and rinsed with distilled water. The glass wool was then soaked for eight days with three distilled water rinses and buffer changes. The buffer from the final soak was assayed for catalase activity by adding an equal volume of 0.2 percent H$_2$O$_2$ and measuring the change in hydrogen peroxide concentration using a spectrophotometric assay; no catalase activity was detected. The glass wool containing catalase bonded to DIMA was then placed in 50 mL of 0.2% hydrogen peroxide solution. The absorbance at 240 nanometers (nm) of the solution was measured using a Hewlett-Packard spectrophotometer at reaction times of about two minutes and at thirty minutes. The absorbance at 240 nm was found to be 0.5 and 0.02, respectively, indicating about 0.03% and less than 0.002% hydrogen peroxide remaining, respectively, using a standard curve of hydrogen peroxide concentration vs. absorption. This result shows that catalase was immobilized on the DIMA treated support and hydrogen peroxide was reduced to a negligible concentration after thirty minutes.

EXAMPLE 2

To a 20 mg sample of carefully cleaned 2 mm diameter glass beads in a chromatography column was added 10 mL of 0.06% of the dimethylamine adduct of epoxidized polybutadiene (DIMA). The mixture was stored for 1.5 hours at about 20° C., then for about 16 hours at 4° C. The solution was eluted from the beads by 40 mL of a phosphate-buffered solution of 10 mg per mL of catalase which was added to the beads. The mixture was stored at 4° C. for about 16 hours and the beads were rinsed with phosphate buffer until no catalase activity was detected in the rinse. The buffer was replaced with 20 mL of 0.2% hydrogen peroxide solution, followed by 20 mL of buffer flowing at a rate of 1 to 2 drops per second. The absorbance of a 2 mL aliquot from the 40 mL of combined eluents was measured and found to be 0.001, which corresponds to less than 0.001% hydrogen peroxide present. A column treated with catalase, but using no protein immobilizer, showed an absorbance at 240 nm of 0.72 corresponding to 0.06 percent hydrogen peroxide.

The data show that greater enzyme activity is observed when DIMA was used to immobilize the protein to the beads.

EXAMPLE 3

To two porous glass discs (35 mm diameter, No. 5, 5 to 50 micrometer pore size) was added enough of an aqueous solution of 0.5% of the dimethylamine adduct of epoxidized polybutadiene to cover the discs. After soaking for 16 hours the solution was decanted and the discs were rinsed with distilled water, then air dried. The discs were then soaked in enough phosphate buffered aqueous solution of 10 mg per mL of catalase to cover for three hours. The solution was decanted from the discs, the discs were rinsed with distilled water, then repeatedly soaked and rinsed in phosphate buffer for eight days until the buffer used for soaking contained no catalase activity. The ability of the discs to reduce hydrogen peroxide was measured by soaking the discs in 10 mL of 0.2% hydrogen peroxide solution and measuring the absorbance at 240 nm at various time intervals. The values for absorbance obtained are shown in Table I.

TABLE I

| Disc | Absorbance at 240 nm | | | |
|---|---|---|---|---|
| No. | 15 Seconds | 5 Minutes | 30 Minutes | 130 Minutes |
| 1 | 1.13 | 0.06 | 0.12 | 0.13 |
| 2 | 2.15 | 1.40 | 0.14 | 0.08 |

The data of TABLE I show that the enzyme was immobilized on the glass discs by DIMA as the immobilizing agent and the enzyme had retained activity.

EXAMPLE 4

Pads of nonwoven web of both an embossed and a mat form of copolyester of 80/20 polyethylene terephthalate and polyethylene isophthalate, nylon 66, and thermally bonded polyethylene terephthalate (PET) (1.0 g each) were dipped in an amine stabilized sol of silicon dioxide (Nalco 2326, Nalco Chemical Co., Oak Brook, IL) containing 1.5% silicon dioxide in ethanol, then the pads were dried at 60° C. for about 15 minutes. The pads (see TABLE II, below) were cut into pieces weighing 0.1 to 0.3 g, then soaked for six hours in 20 mL of 0.06% aqueous solution of the dimethylamine adduct of epoxidized polybutadiene (DIMA). The pads were drained, then rinsed with distilled water. The pads were soaked in 10 mL of an aqueous phosphate-buffered solution of 1 mg per mL of catalase for sixteen hours at 4° C. and at about 20° C. for 1.5 hours. The pads were soaked in buffer, drained and rinsed with distilled water until no catalase activity could be detected in the washings. A nonwoven polypropylene pad was prepared similarly, but the soaking time in DIMA solution was 16 huurs and in catalase solution 24 hours. All of the drained pads were soaked in 10 mL of 0.2% hydrogen peroxide solution and the absorbance of the solution was measured initially (at less than 15 seconds) and after 30 minutes. If a two-container system is used for contact lens disinfection, and volume of saline in the second container is 10 mL, the hydrogen concentration in the second container is assumed to be ~0.2%.

TABLE II

| | Absorbance at 240 nm | | | | | |
|---|---|---|---|---|---|---|
| Pad | 15 sec. | 1 min. | 5 min. | 15 min. | 30 min. | 60 min. |
| A. embossed copolyester (0.24 g) | 2.11 | 1.74 | 0.76 | 0.04 | 0.01 | — |
| B. embossed copolyester (0.24 g) | 2.08 | 1.57 | 0.56 | 0.05 | 0.01 | — |
| C. nylon 66 (0.14 g) | 0.82 | 0.62 | 0.05 | — | 0.03 | — |
| D. thermally bonded PET (0.14 g) | 1.72 | 0.92 | 0.21 | 0.07 | 0.02 | — |
| E. PET mat (0.13 g) | 1.83 | 1.80 | 0.97 | 0.28 | 0.14 | 0.02 |
| F. copolyester mat (0.14 g) | 1.74 | 0.18 | 0.69 | 0.15 | 0.11 | 0.02 |
| G. copolyester mat (0.12 g) | 1.97 | 1.45 | 0.61 | 0.10 | 0.09 | — |
| H. polypropylene (0.3 g) | 2.47 | — | 0.77 | 0.54 | 0.47 | — |

The data of TABLE II show that the absorbance decreased from a maximum of 2.5 to a minimum range of 0.01 to 0.50 in 30 minutes. These values correspond to a decrease in hydrogen peroxide concentration from about 0.15% to less than 0.001%.

The data show the article is efficacious in removing hydrogen peroxide to a negligible level if used in a two-container system.

The soaked pads were then resoaked with 10 mL of 3% hydrogem peroxide solution and the absorbance at 240 nm of the solution was measured at timed intervals. The data are shown in TABLE III below.

TABLE III

| | Absorbance at 240 nm | | | | | |
|---|---|---|---|---|---|---|
| Pad | 15 sec. | 5 min. | 15 min. | 30 min. | 60 min. | 90 min. |
| A. embossed copolyester (0.24 g) | 3.12 | 0.05 | 0.05 | — | — | — |
| B. nylon 66 mat (0.14 g) | 0.45 | 0.05 | 0.06 | — | — | — |
| C. thermally bonded PET (0.14 g) | 3.10 | 0.12 | 0.11 | 0.12 | — | 0.12 |
| D. PET mat (0.15 g) | 3.15 | 2.99 | 3.02 | — | 3.17 | — |
| E. copolyester mat (0.12 g) | 3.05 | 0.24 | 0.10 | 0.07 | — | — |
| F. polypropylene mat (0.3 g) | >4.0 | 2.17 | 0.07 | 0.06 | — | — |

The data of TABLE III show that the articles used bound sufficient catalase concentration on a small pad to decompose 3% hydrogen peroxide. Also, these data show that the article can be reused and can remove hydrogen peroxide to a negligible level if used in a one container system.

EXAMPLE 5

The copolyester pad used in Example 4E was placed in a 10 mL sample of 3% hydrogen peroxide in 0.01M phosphate buffer, at pH 9.0, and the absorbance of the solution was measured at a wavelength of 240 nanometers at time intervals as shown in TABLE IV. After 90 min., the pH of the solution was 10.0, and after 16 hours, the pH was 8.7.

The nylon pad of Example 4B and the copolyester pad of Example 4A were placed in 10 mL samples of 3% hydrogen peroxide 0.01M phosphate buffer at pH 4.7, and the absorbance of the solution was measured at time intervals as shown in TABLE IV. After 90 minutes the pH of the solution containing the nylon pad was 6.2 and the copolyester pad was 5.8. The pads were rinsed with phosphate buffer, pH 7.25, drained and resoaked in 10 mL 3% hydrogen peroxide in phosphate buffer at pH 7.4 and absorbance at 240 nm was measured at time intervals (TABLE IV). The pH of solutions containing the nylon and copolyester mats were 7.4 and 7.2, respectively, after 10 minutes of reaction time.

TABLE IV

|  | 15 sec. | 5 min. | 15 min. | 30 min. | 60 min. |
|---|---|---|---|---|---|
| A. copolyester mat | | | | | |
| pH 9.0 | 3.15 | 0.19 | 0.17 | 0.16 | 0.14 |
| 7.4 | 3.15 | 3.07 | 3.09 | 3.07 | — |
| B. copolyester, embossed | | | | | |
| pH 4.7 | 3.14 | 0.07 | 0.11 | 0.11 | 0.09 |
| 7.4 | 3.14 | 1.4 | 0.22 | 0.05 | — |
| C. nylon mat | | | | | |
| pH 4.7 | 3.06 | 0.16 | 0.14 | 0.12 | 0.11 |
| 7.4 | 3.04 | 0.38 | 0.02 | 0.02 | — |

These trials show that the method of the invention was efficacious under both acidic and basic conditions and remained useful even after cycling in an acidic solution of hydrogen peroxide.

EXAMPLE 6

A polypropylene pad weighing about 0.2 g containing catalase bonded to DIMA, prepared as described in Example 4, was refrigerated at 4° C. for one hour and then immersed in 10 mL of 3% hydrogen peroxide solution also at 4° C. The absorbances measured at <10 sec., 15 min., and 2½ hours were greater than 4, 0.09 and 0.04, respectively, indicating greater than 0.2%, and about 0.005% and 0.004% concentrations of hydrogen peroxide remaining.

The data show that the method of the invention works at relatively cold temperatures suitable for the storage of catalase.

EXAMPLE 7

An embossed polypropylene pad prepared according to the method of Example 4 was stored for two days at 4° C. in a desiccator. The pad was then soaked in 10 mL of buffer for 15 minutes at room temperature. The solution was decanted and the pad immersed in 10 mL of 3% hydrogen peroxide solution. The absorbance at 240 mm of the solution was measured using the method of Example 1. For the pad stored dry, the average absorbance initially was greater than 4 and decreased to 0.009 at 60 minutes, corresponding to hydrogen peroxide concentrations of greater than 0.2% and less than 0.004%, respectively.

The data showed that the method of the invention is operative even after the composite article had been dried and rehydrated.

EXAMPLE 8

Pads of various nonwoven webs as described in Example 4 weighing 0.1 to 0.2 g were dipped in an amine stabilized sol of silicon dioxide (Nalco 2326, Nalco Chemical Company, Oak Brook, IL) containing 1.5% silicon dioxide in ethanol, then the pads were drained and dried at 60° C. for about 15 minutes. The dry pads were soaked for 24 hours, each pad in 10 mL of 0.5% of silane-treated polycarbodiimide in toluene at about 20° C. The pads were then rinsed with 20 mL of toluene, air dried in a fume hood for 16 hours and cured by heating for 15 minutes at 60° C. The pads were each soaked in 3 mL of a 10 mg/mL solution of catalase for 4 hours at about 20° C., rinsed with distilled water and soaked in phosphate buffer (pH 7) for about 16 hours. The pads were rinsed again with distilled water and soaked in buffer for another 16 hours. No catalase activity was detected in the soaking solution. Each of the pads was then immersed in 10 mL of 0.2% hydrogen peroxide solution and the absorbance of the solution was measured at various time intervals using the method described in Example 1 as shown in Table V.

TABLE V

| Pad | Absorbance at 240 nm | | | | | |
|---|---|---|---|---|---|---|
| | 10 sec. | 5 min. | 15 min. | 30 min. | 60 min. | 90 min. |
| A. embossed copolyester (0.19 g) | 2.22 | 1.89 | 1.37 | 1.00 | 0.62 | 0.35 |
| B. embossed copolyester (0.16 g) | 2.36 | 2.07 | 1.55 | 1.04 | 0.72 | 0.60 |
| C. nylon 66 (0.07 g) | 2.04 | 2.03 | 1.50 | 1.23 | 0.94 | 0.82 |
| D. thermally bonded PET (0.08 g) | 2.31 | 1.90 | 1.29 | 0.76 | 0.77 | 0.29 |
| E. copolyester mat (0.11 g) | 1.98 | 1.76 | 1.39 | 1.04 | 0.67 | 0.67 |
| F. copolyester mat (0.09 g) | 2.04 | 1.60 | 0.98 | 0.80 | — | — |

These data show that the absorbance decreased to less than 1.0 in 60 minutes which corresponds to a hydrogen peroxide concentration of less than 0.05 percent. The data show that coupling agents other than DIMA are useful in the construction of the invention.

EXAMPLE 9

Pads of nonwoven web of polypropylene and nylon 66 were soaked for 24 hours in about 25 mL of a 0.06% solution of the dimethylamine adduct of epoxidized polybutadiene at about 20° C. The pads were rinsed with distilled water. The pads were then soaked in 25 mL of a solution of catalase (1 mg per mL in 0.01M phosphate buffer pH 7.2) for 3 hours at 4° C. and 2.5 hours at about 20° C. The pads were alternately soaked in buffer, drained and rinsed with distilled water overnight until no catalase activity could be detected in the washings.

A companion set of pads was prepared as controls in a similar manner but a ceramic-precursor gel layer was applied by dipping the nonwoven pads in 1.5% amine stabilized sol of silicon dioxide (Nalco 2326) at a ratio of about 0.1 g silicon oxide to 1.25 g nonwoven fibers. The nylon and polypropylene pads were dried at about 60° C. for fifteen minutes. A 10 mL portion of 3% hydrogen peroxide in 0.01M phosphate buffer, pH 7.2, was added to each pad and the decomposition of hydrogen peroxide solution was monitored by recording the absorbance at 240 nm of the solution at time intervals up to at least thirty minutes. See TABLE VI (A-D). The nylon pads were soaked for about 65 hours with 2 buffer changes, then drained and resoaked in 10 mL of 3% $H_2O_2$. The decompositin was monitored as stated above. See TABLE VI (E and F).

TABLE VI

| Pads all with DIMA | Weight | Absorbance at 240 nm | | | | |
|---|---|---|---|---|---|---|
| | | 15 seconds | 1 minute | 5 minutes | 15 minutes | 30 minutes |
| A. polypropylene + SiO$_2$ | 0.10 | >4 | >4 | 1.97 | 0.91 | 0.24 |
| B. polypropylene, no SiO$_2$ | 0.18 | >4 | >4 | >4 | >4 | >4 |
| C. nylon 66 + SiO$_2$ | 0.10 | >4 | 0.816 | 0.22 | 0.10 | 0.04 |
| D. nylon 66, no SiO$_2$ | 0.12 | >4 | >4 | — | — | — |
| E. nylon 66, + SiO$_2$ | 0.10 | — | 3.20 | 2.81 | 1.80 | 0.09 |
| F. nylon 66, no SiO$_2$ | 0.12 | — | 3.17 | 3.19 | — | 3.15 |

The data of TABLE VI show that the polypropylene pad without ceramic-precursor gel coating showed no detectable enzymatic activity within thirty minutes, and the nylon pad without ceramic-precursor gel coating showed reduced enzymatic activity within thirty minutes.

EXAMPLE 10

Embossed copolyester (80% polyethylene terephthalate 20% polyethylene isophthalate) nonwoven pads were prepared as in Example 9 with no DIMA coating. A companion copolyester pad was prepared with a DIMA coating as a control. The decomposition of 3% H$_2$O$_2$ solution was measured in the usual manner (see Example 9). The data are shown in Table VII.

TABLE VII

| Pads with SiO$_2$ | Absorbance at 240 nm | | | | |
|---|---|---|---|---|---|
| | 15 sec. | 1 min. | 5 min. | 15 min. | 30 min. |
| Embossed copolyester with DIMA (3.5 × 3.5 cm) | >4 | — | 3.07 | 0.77 | 0.45 |
| Embossed copolyester, no DIMA (3.5 × 3.5 cm) | >4 | 3.26 | 3.37 | 3.15 | 3.13 |

The data of TABLE VII show significant increase in retained catalase activity when the DIMA-coated web was used.

EXAMPLE 11

A cellulose pad (No. 2 Whatman TM filter paper) and nylon chiffon were coated with silicon dioxide, DIMA, and catalase as described in Example 9.

A pad of alumina-boria-silica 3:1:2 ceramic fiber (Nextel 321 TM, 3M, St. Paul, Minn.) was coated with DIMA and catalase as described above in Example 9. The absorbance data are shown in TABLE VIII below.

TABLE VIII

| | Weight (in g) | Absorbance at 240 nm | | | |
|---|---|---|---|---|---|
| | | 1 min. | 5 min. | 15 min. | 30 min. |
| cellulose | 0.65 | 3.18 | 0.22 | 0.20 | 0.22 |
| woven nylon | 0.64 | >4 | 0.57 | 0.71 | 0.17 |
| Nextel | 1.36 | >4 | 1.03 | — | 0.11 |

The data of TABLE VIII for absorbance show detectable bound catalase on supports other than synthetic nonwovens when these samples were tested with 10 ml of 3% hydrogen peroxide.

EXAMPLE 12

Catalase was bound to a nonwoven polyethylene terephthalate pad which was provided with DIMA and gel coatings as described in Example 4. Pads were sterilized with ethylene oxide at 29° C. and degassed at 4° C. for several days.

Ten polyvinylpyrrolidone/HEMA lenses (Softcon TM, American Optical, 55% water content soft contact lenses) were inoculated with sixty five million Pseudomonas aeruginosa (American Type Culture Collection (ATCC) #27853) colony forming units (cfu). Two lenses were cleaned with Bausch and Lomb Daily Cleaner TM and microorganisms were eluted from each lens with 5% Tween-80 TM, saline solution with non-ionic surfactant (ICI Americas, Inc.) and plated on tryptic soy agar. About eight thousand cfu's of the Pseudomonas aeruginosa were present on the lenses before hydrogen peroxide disinfection. Eight of the ten lenses were cleaned with Bausch and Lomb Daily Cleaner TM and rinsed with sterile saline and placed in lens holders.

In a two-container, two-step system, a lens was inserted into each of two containers containing 10 mL of 3% hydrogen peroxide, in 0.01M phosphate buffer, pH 7.2, for 10 minutes, removed and reinserted into vials containnng 10 mL of phosphate buffer and a 0.13 g polyester (PET) pad with immobilized catalase and soaked for four hours. In a one-container, one-step system, a lens was inserted into each of two containers containing 10 mL of 3% hydrogen peroxide in phosphate buffer with 0.15 g polyester pads with immobilized catalase and soaked for 4 hours. Two lenses were disinfected and neutralized as directed in two Septicon TM Catalytic Disinfection Systems, which requires soaking lenses in about 10 mL of Lensept (3% H$_2$O$_2$) solution for ten minutes, removal, and reinsertion in a second container with about 10 mL of Sensitive Eyes Saline solution with a platinum coated disc for four hours. Two lenses were placed in 10 mL of sterile saline for four hours. The eight treated lenses were removed from the disinfection containers, then placed in ten ml of tryptic soy broth, and incubated at 35° C. for 6 days. The final soaking solutions were transferred to 100 mLs of broth and incubated 6 days at 35° C. At the end of the 6-day incubation, containers of broth were scored for the presence of visible turbidity in the solutions. Visible turbidity of the incubated broth indicated lack of disinfection (+). The results are shown in Table IX.

TABLE IX

| Sample | System | Lens | Soak Solution |
|---|---|---|---|
| 1 | 2-step, 2-container catalase | — | — |
| 2 | 2-step, 2-container catalase | — | — |
| 3 | 1-step, 1-container catalase | — | — |
| 4 | 1-step, 1-container catalase | — | — |
| 5 | Septicon | — | + |
| 6 | Septicon | — | — |
| 7 | saline only | + | + |
| 8 | saline only | — | + |

The data of TABLE IX show that one lens without hydrogen peroxide disinfection was not disinfected.

The saline soaks from both lenses showed microbial growth. The Sensitive Eyes soaking solution from one of the Septicon systems also showed microbial growth. The catalase one-step, one-container, and two-step, two-container, systems resulted in disinfected lenses and the soak solutions showed no microbial growth.

The data of TABLE IX show that the method of the invention can be used in a one-step, one-container system, and also in a two-step, two-container system.

EXAMPLE 13

Polypropylene blown microfiber (BMF) was placed in a plasma treatment chamber that was equipped with two (23 cm×33 cm) substantially parallel aluminum electrodes. The material to be treated was placed on the non-driven electrode and the system evacuated to 10 millitor. The system was then backfilled with 0.5 torr carbon dioxide ($CO_2$) and a plasma ignited with a Plasmalac TM (ENI, Inc.) generator with A.C. power at 25 KHz and at 200 watts. The plasma treatment was run for 0.5 min. After treatment the sample was brought to atmospheric pressure.

The trial was repeated using air at 1.0 torr pressure as the gas in the plasma treatment chamber.

Pads were cut from the treated BMF and were weighed and soaked 6 hours at room temperature in 0.05% DIMA solution. The pads were rinsed, drained, and soaked 16 hours at 4° C. in 0.1 mg catalase/mL in phosphate buffer. The measured free catalase activity was 48,000 units/mg. The pads were soaked and rinsed until no free catalase was detected in the soaking solution.

The pads were soaked in 10 mL of 3% $H_2O_2$ solution and absorbance monitored at 240 nm as a function of time. The data are shown in TABLE X below.

TABLE X

| Plasma gas | Absorbance at 240 nm | | | | |
| --- | --- | --- | --- | --- | --- |
| | <15 sec. | 5 min. | 15 min. | 30 min. | 60 min. |
| $CO_2$ | >4.0 | 2.51 | 0.15 | 0.01 | 0.01 |
| air | >4.0 | 3.30 | 0.65 | 0.19 | 0.01 |

The data show that a plasma treatment can produce binding sites for protein immobilizers on BMF pads, and that the plasma treatment is useful in the construction of the present invention.

Various modifications and alterations of this invention will become apparent to those skilled in the art without departing from the scope and spirit of this invention, and it should be understood that this invention is not to be unduly limited to the illustrative embodiments set forth herein.

We claim:

1. A method for disinfecting a medical device comprising the steps:
   (a) immersing a medical device in a hydrogen peroxide solution for a time sufficient to disinfect said device,
   (b) decomposing any residual hydrogen peroxide by use of a catalytically effective amount of a protein capable of decomposing hydrogen peroxide, said protein being immobilized on a composite article, comprising in sequence:
      (1) a polymeric fibrous support, wherein said support has been subjected to a surface modification treatment to provide binding sites thereon, said treatment providing a layer of inorganic oxide having a uniform thickness when dried in the range of 2 to 500 nm to provide binding sites thereon, or being a radio frequncy or microwave plasma treatment carried out at a frequency of 10 to 125 kilohertz with a power density in the range of 0.05 to 2.25 w/cm² generated between two electrodes in a gas at a pressure in the range of 10 mtorr to 10 torr,
      (2) a layer of a protein immobilizer compound comprising a polymer or a silane-functional compound, and
      (3) a biological active protein bound to said layer of protein immobilizer compound and capable of decomposing hydrogen peroxide.

2. The method according to claim 1 wherein said support is a woven or nonwoven web.

3. The method according to claim 2 wherein said support is a nonwoven web.

4. The method according to claim 1 wherein said support is selected from the group consisting of polyalkylenes, polyvinyl chlorides, polyamides, polyvinyl alcohols, polystyrenes, polyarylsulfones, polyesters, polycarbonates, polyacrylates, cellulosics, polyurethanes, and combinations thereof.

5. The method according to claim 4 wherein said support is polyester, nylon, or polypropylene.

6. The method according to claim 5 wherein said polyester is polyethylene terephthalate.

7. The method according to claim 1 wherein said treatment provides a layer of a gelled network of inorganic oxide particles.

8. The method according to claim 1 wherein said surface modification treatment provides a layer of a ceramic-precursor sol.

9. The method according to claim 1 wherein said treatment is a plasma treatment.

10. The method according to claim 1 wherein said protein immobilizer compound is a beta-hydroxyalkyleneamine-containing polymer.

11. The method according to claim 1 wherein said protein immobilizer compound is an amine adduct of epoxidized poly-cis-1,4-butadiene, epoxidized styrene/cis-1,4-butadiene, or polyglycidyl methacrylate.

12. The article according to claim 11 wherein said amine is dimethylamine, diethylamine, morpholine, piperidine, or n-propylamine.

13. The method according to claim 1 wherein said protein is catalase or peroxidase.

14. The method according to claim 13 wherein said protein is catalase.

15. A method of disinfecting a medical device comprising the steps:
   (a) immersing a medical device in a hydrogen peroxide solution for a time sufficient to disinfect said device,
   (b) decomposing any residual hydrogen peroxide by use of a catalytically effective amount of catalase, said catalase being immobilized on a composite article, said composite article comprising in sequence:
      (1) a polymeric woven or nonwoven fibrous support, wherein said support has been sujected to a surface modification treatment to provide binding sites thereon, said treatment providing a layer of inorganic oxide having a uniform thickness when dried in the range of 2 to 500 nm to provide binding sites thereon, or being a radiowave or microwave plasma treatment carried out at a frequency of 10 to 125 kilohertz with a power density in the range of 0.05 to 2.25 w/cm² generated between two electrodes in a gas at a pressure in the range of 10 mtorr to 10 torr, (2) a layer of a protein immobilizer compound comprising a polymer or a silane-functional compound, and (3) catalase bound to said layer of protein immobilizer compound.

16. The method according to claim 15 wherein said surface modification treatment provides a layer of a gelled network of inorganic oxide particles.

17. The method according to claim 15 wherein said surface modification treatment is a plasma treatment.

18. A kit for disinfecting a medical device wherein hydrogen peroxide is the disinfecting agent, said kit comprising in one package an amount of hydrogen peroxide solution sufficient to disinfect said device and a composite article comprising in sequence:

(1) a polymeric fibrous support, wherein said support has been subjected to a surface modification treatment to provide binding sites thereon, said treatment providing a layer of inorganic oxide having a uniform thickness when dried in the range of 2 to 500 nm to provide binding sites thereon, or being a radiowave or microwave plasma treatment carried out at a frequency of 10 to 125 kilohertz with a power density in the range of 0.05 to 2.25 w/cm² generated between two electrodes in a gas at a pressure in the range of 10 mtorr to 10 torr, (2) a layer of a protein immobilizer compound comprising a polymer or a silane-functional compound, and (3) a biologically active protein selected from the group consisting of catalase and peroxidase bound to said layer of protein immobilizer compound.

19. A kit for disinfecting a medical device wherein hydrogen peroxide is the disinfecting agent, said kit comprising the combination of a first package containing an amount of hydrogen peroxide solution sufficient to disinfect said device, and a second package containing a composite article comprising in sequence:

(1) a polymeric fibrous support, wherein said support has been subjected to a surface modification treatment to provide binding sites thereon, said treatment providing a layer of inorganic oxide having a uniform thickness when dried in the range of 2 to 500 nm to provide binding sites thereon, or being a radiowave or microwave plasma treatment carried out at a frequency of 10 to 125 kilohertz with a power density in the range of 0.05 to 2.25 w/cmhu 2 generated between two electrodes in a gas at a pressure in the range of 10 mtorr to 10 torr, (2) a layer of protein immobilizer compound comprising a polymer or a silane-functional compound, and (3) a biologically active protein selected from the group consisting of catalase and peroxidase bound to said layer of protein immobilizer compound.

* * * * *